United States Patent [19]

Stack et al.

[11] Patent Number: 4,732,983

[45] Date of Patent: Mar. 22, 1988

[54] PYSCHOTROPIC POLYCYCLIC IMIDES

[75] Inventors: Gary P. Stack, Merion; Guy A. Schiehser, Malvern, both of Pa.; Magid A. Abou-Gharbia, Wilmington, Del.

[73] Assignee: American Home Products Corporation, New York, N.Y.

[21] Appl. No.: 34,522

[22] Filed: Apr. 3, 1987

[51] Int. Cl.[4] .................. C07D 401/14; C07D 403/14; C07D 403/04; C07D 403/06

[52] U.S. Cl. ................................. 544/295; 544/333; 544/334; 544/335; 544/361; 544/372; 544/364; 544/363; 544/331; 544/332

[58] Field of Search ............... 544/295, 333, 334, 335, 544/361, 372, 364, 363

[56] References Cited

FOREIGN PATENT DOCUMENTS 2057845  6/1971  Fed. Rep. of Germany .
6087262  5/1985  Japan .
7017031  11/1969  Netherlands .

Primary Examiner—John M. Ford
Attorney, Agent, or Firm—Richard K. Jackson

[57] ABSTRACT

Substituted imides of the following formulae are antipsychotic, anxiolytic agents with very little extrapyramidal side effects:

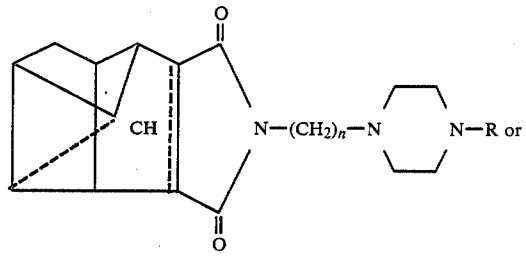

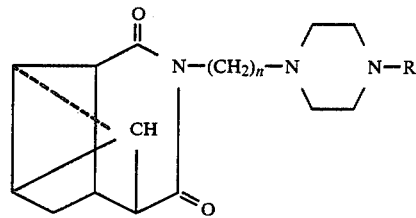

in which n is one of the integers 2, 3, 4 or 5; R is phenyl, halophenyl, trifluoromethylphenyl, alkoxyphenyl in which the alkoxy substituent contains 1 to 3 carbon atoms, 2-pyrimidinyl halopyrimidin-2-yl, 2-pyrazinyl, halopyrazin-2-yl, 2-pyridinyl, halopyridin-2-yl, cyanopyridin-2-yl, quinolyl, or haloquinolyl; and the dotted lines represent optional unsaturation; or a pharmaceutically acceptable salt thereof.

8 Claims, No Drawings

PYSCHOTROPIC POLYCYCLIC IMIDES

BACKGROUND OF THE INVENTION

Netherlands Pat. No. 7,017,031 discloses 8-(heteroarylpiperazinylalkyl)-8-azaspiro[4,5]decane-7,9-diones as transquilizers and anti-emetics.

Japanese Pat. No. 60/87262 (C.A. 103: 215155K) discloses N-(heteroarylpiperazinylalkyl)cycloalkanosuccinimide derivatives as having anti-conflict activity.

DESCRIPTION OF THE INVENTION

In accordance with this invention there is provided a group of antipsychotic anxiolytic N-(aryl and heteroarylpiperazinylalkyl)polycyclic dicarboxylic acid imides of the formulae:

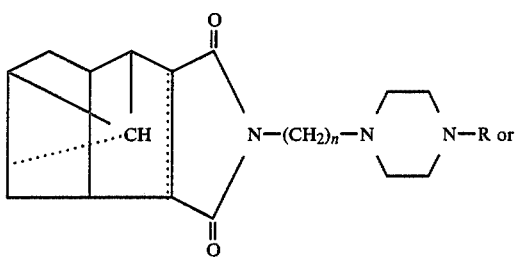

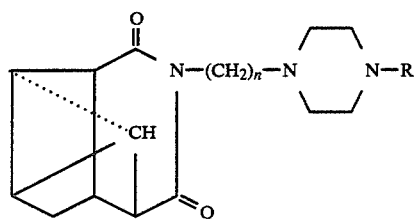

in which
  n is one of the integers 2, 3, 4 or 5;
  R is phenyl, halophenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridyl, halopyridin-2-yl, cyanopyridin-2-yl, quinolyl, or haloquinolyl;

and the dotted lines represent optional unsaturation; or a pharmaceutically acceptable salt thereof. In the first depicted structure, the succinimide ring juncture is either endo or exo with respect to either of the bicyclic rings.

Of the halogen substituents fluoro, chloro and bromo appearing in R, chloro is preferred. The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of the invention are prepared by conventional methods. For example, a suitable polycyclic dicarboxylic acid, or the anhydride derived from it, is combined with the desired piperazinyl alkyl amine in a high boiling solvent such a toluene or xylene and refluxed for an extended period with either chemical (e.g. ethoxyacetylene) or mechanical (e.g. Dean-Stark trap) water removal, as illustrated with the 4,5,7-methenopentaleno compounds, thusly:

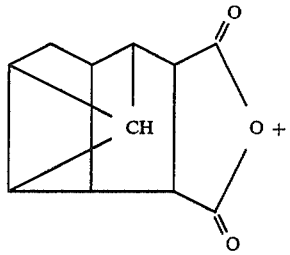

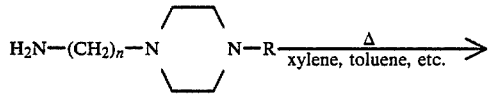

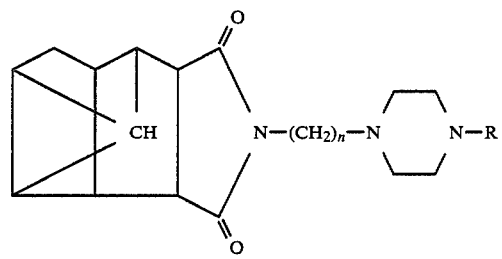

Alternatively, the compounds of this invention are readily prepared from the appropriate polycyclic imide via alkylation with a suitable dihalo lower alkane in the presence of a strong base such as sodium hydride, followed by reaction of the intermediate product with the desired aryl- or heteroaryl substituted piperazine, thusly:

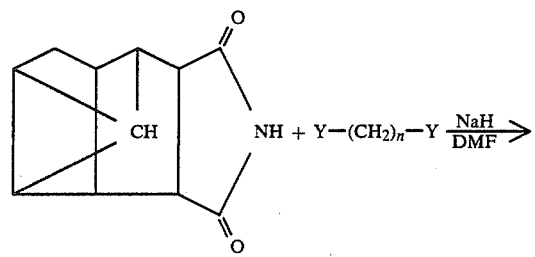

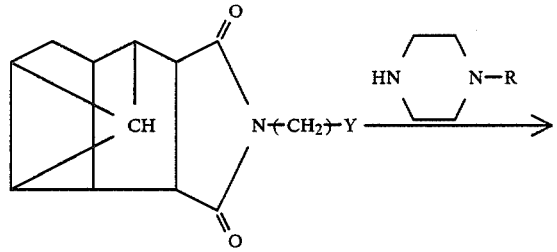

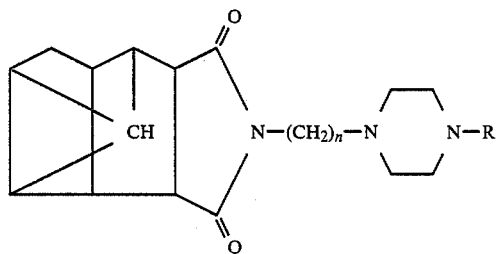

where Y is chlorine or bromine.

The polycyclic dicarboxylic acids themselves are known compounds or they can be prepared from the appropriate polycyclic olefin by treatment with a suitable oxidizing agent such as potassium permanganate or ruthenium tetroxide (or from the appropriate polycyclic ketone by treatment with potassium permanganate or potassium trioxide or from the appropriate diketone via treatment with periodic acid).

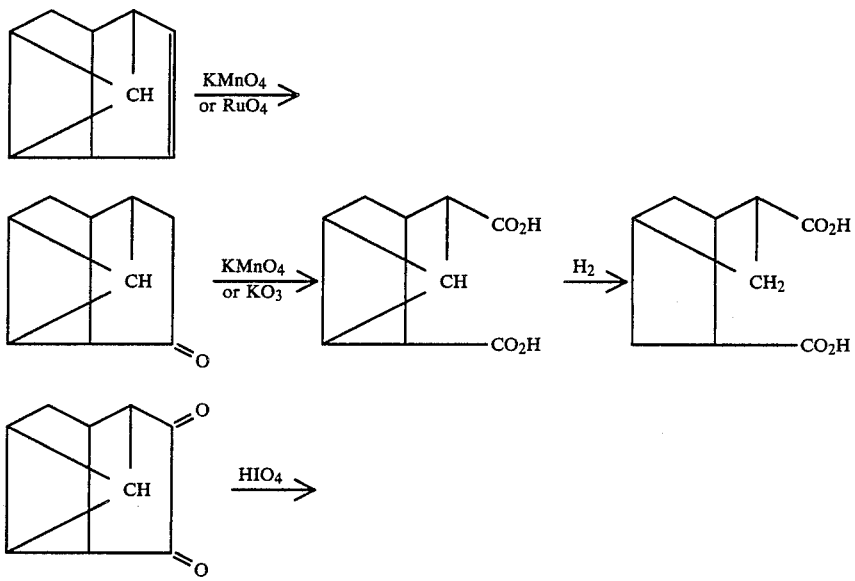

Hydrogenation of the tricyclicdicarboxylic acid affords the bicyclic carboxylic acid.

The antipsychotic properties of the compounds of this invention were established by standard pharmacologically accepted procedures involving conditioned avoidance studies in which trained male CD rats (Charles River), 400-450 g. body weight are exposed to a fifteen second warning tone (conditioned stimulus) continued for an additional fifteen seconds accompanied by electric shock. The rat can avoid the electric shock by jumping to an exposed shelf (shelf-jump response). A response during the initial warning tone is considered an avoidance response, while a response during shock delivery is considered as escape response. The shelf-jump response test procedure follows that of Herman et al., Comm. in Psychopharm., 3, pp. 165–171 (1979). The compounds of this invention were tested at a single dose (40 mg./kg. i.p.) in this procedure and were rated relative to their inhibition of conditioned avoidance responding. A similar test procedure in which a lever press was substituted for a shelf-jump was used to establish the oral (p.o.) activity of the test compounds. Orally active compounds were tested over a full dose range and the Avoidance Block activities reported as "$AB_{50}$'s" (mg./kg.).

As a further measure of antipsychotic activity, the compounds of this invention were also studied as antagonists of apomorphine-induced stereotyped behavior and climbing wherein CF-1 mice (Charles River) receive the test compound i.p. at several dose levels (1, 10, 30 and 60 mg./kg.) (six mice per dose level) and thirty minutes later receive 1 mg./kg. apomorphine s.c. Five minutes after injection, the sniffing-licking-gnawing syndrome and climbing behavior induced by apomorphine are scored for each animal. Readings are repeated every five minutes during a thirty minute test session.

An $ED_{50}$ value (with 95% confidence intervals) is calculated for inhibition of apomorphine-induced stereotyped behavior and climbing using a non-linear least squares calculation with inverse prediction. The ratio of the $ED_{50}$ for stereotyped behavior to the $ED_{50}$ for climbing is calculated. High ratios indicate antipsychotic activity with low ability for the extrapyramidal side effects which attend long term treatment with such standard antipsychotic drugs as haloperidol (ratio=1.00), chlorpromazine (ratio=1.51) and thioridazine (ratio=1.83).

In further support of the low potential for side-effects exhibited by the compounds of this invention, representative compounds were established to exhibit only weak binding to the D-2 dopamine receptor when tested in accordance with a modification of the procedure of Fields et al., Brain Res., 136, pp. 578–584 (1977) and Yamamura et al., eds., Neurotransmitter Receptor Binding, Raven Press, N.Y. (1978), wherein homogenized limbic brain tissue is incubated with $^3H$-spiroperidol and various concentrations of test compound, filtered and washed and shaken with Hydrofluor scintillation cocktail (National Diagnostics) and counted in a Packard 460CD scintillation counter. The results of this testing with compounds representative of the invention whose production is exemplified, infra, are as follows:

| | Conditioned Avoidance | | Apomorphine Antagonism $ED_{50}$, mg/kg, p.o. | | [$^3H$] Spiroperidol Binding Inhibition |
|---|---|---|---|---|---|
| Ex. | Shelf-Jump 40 mg/kg i.p. | Discrete Trial $AB_{50}$ p.o. | Stereo-typy | Climbing | Ki, nM or % at 1 μM |
| 1 | ~80% | 55.68 | inactive | 17.0 | 76% |
| 2 | >20% | active | inactive | 15.61 | 0% |
| 3 | >20% | 46.77 | inactive | 18.99 | 44% |
| 4 | >20% | 56.16 | inactive | inactive | 54% |
| 5 | ~80% | inactive | inactive | inactive | 25% |
| 6 | ~80% | active | 40.46 | 1.74 | 29% |
| 7 | ~80% | weak | inactive | inactive | 51% |

From these data, the activity profile of the compounds of this invention are seen to be that of antipsychotic agents with less potential for extra pyramidal side effects such as attend the use of major tranquillizers (sedation, pseudoparkinsonism, ataxia, muscle relaxation, etc.). This activity profile resembles that of the anxiolytic compound, buspirone. Further evidence that the pharmacological profile of the test compounds resembles that of buspirone was obtained by measuring the compound's ability to displace [$^3$H]8-OH DPAT (dipropylaminotetralin) from the 5-HT$_{1A}$ serotonin receptor by the procedure of Hall et al., *J. Neurochem.* 44: 1685-1696, 1985. Compounds of the invention, like buspirone, exhibited potent affinity for this serotonin receptor subtype. The anxiolytic activity of buspirone is currently believed to be due, at least in part, to this receptor (Vander Maclen et al., *Eur. J. Pharmacol.* 1986, 129 (1-2) 123-130. The test results of this study are as follows:

| Example | Inhibition of [$^3$H] 8-OH DPAT Binding Ki, nM or % at 1 μM |
|---------|------------------------------------------------------------|
| 1 | 12.8 nM |
| 2 | 40.0 nM |
| 3 | 41.9 nM |
| 4 | 76% |
| 5 | 94.0 nM |
| 6 | 51.0 nM |
| 7 | 16.0 nM |

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

Endo-2-[4-[4-(2-pyrimidinyl)-1-piperazinyl]butyl]octahydro-4,5,7-metheno-1H-pentaleno[1,2-c]pyrrole-1,3(2H)-dione Octahydro-4,5,7-methenopentaleno[1,2-c]furan-1,3-dione (3.8 g., 20 mmoles) was combined with 4.8 g. (20 mmoles) of 1-(4-aminobutyl)-4-(2-pyrimidinyl)piperazine in 300 mL. of xylene and refluxed under nitrogen for 48 hours with water removal via a Dean-Stark trap. The solvent was then removed in vacuo and the residue carefully column chromatographed on 250 g. of silica gel using a gradient elution starting with chloroform and ending with 5% ethanol in chloroform. The slightly more polar major product was crystallized (2 crops) from isopropanol as the free base and then recrystallized again from isopropanol with the addition of 4N HCl/isopropyl alcohol to yield 4.5 g. of a white solid, m.p. 245°-247° C.

Analysis for: $C_{23}H_{29}N_5O_2 \cdot HCl \cdot H_2O$: Calculated: C, 59.80; H, 6.98; N, 15.16. Found: C, 60.15; H, 6.62; N, 15.18.

EXAMPLE 2

Exo-2-[4-[4-(2-pyrimidinyl)-1-piperazinyl]butyl]octahydro-4,5,7-metheno-1H-pentaleno[1,2-c]pyrrole-1,3(2H)-dione The title compound was isolated as the slightly less polar minor product of the chromatography described in Example 1. Recrystallization from ispropanol with the addition of 4N HCl/isopropyl alcohol gave 1.5 g. of white solid, m.p. 198°–203° C.

Analysis for: $C_{23}H_{29}N_5O_2.2HCl.H_2O$: Calculated: C, 55.42; H, 6.67; N, 14.05. Found: C, 55.53; H, 6.36; N, 14.13.

EXAMPLE 3

Endo-2-[4-[4-(6-chloro-2-pyrazinyl)-1-piperazinyl]butyl]octahydro-4,5,7-metheno-1H-pentaleno[1,2-c]pyrrole-1,3-(2H)-dione Octahydro-4,5,7-methenopentaleno[1,2-c]furan-1,3-dione (3.12 g., 16 mmoles) and 1-(4-aminobutyl)-4-(6-chloro-2-pyrazinyl)piperazine (4.0 g., 15 mmoles) were refluxed in 300 mL. of xylene under nitrogen for 48 hours with water removal via a Dean-Stark trap. The solvent was removed in vacuo and the residue carefully column chromatographed on 250 g. of silica gel using a gradient elution starting with chloroform and ending with 5% ethanol in chloroform. Once again, the endo compound was isolated as the more polar major product, and recrystallized from isopropanol with the addition of 4N HCl/isopropyl alcohol to yield 2.8 g of tan solid, m.p. 250°–251° C.

Analysis for: $C_{23}H_{28}N_5O_2Cl.HCl$: Calculated: C, 57.74; H, 6.11; N, 14.64. Found: c, 57.76; H, 5.89 N, 14.50.

EXAMPLE 4

Exo-2-[4-[4-(6-chloro-2-pyrazinyl)-1-piperazinyl]butyl]octahydro-4,57-metheno-1H-pentaleno[1,2-c]pyrrole-1,3-(2H)-dione The title compound was isolated as the less polar minor product of the chromatography in Example 3. Crystallization from isopropanol with the addition of 4N HCl/isopropyl alcohol, followed by recrystallization from isopropanol, gave 800 mg. of white solid, m.p. 228°–230° C.

Analysis for: $C_{23}H_{28}N_5O_2.HCl$: Calculated: C, 57.74; H, 6.11; N, 14.64. Found: C, 57.45; H, 6.08; N, 14.25.

EXAMPLE 5

Endo-2-[4-[4-(2-pyrazinyl)-1-piperazinyl]butyl]octahydro-4,5,7-metheno-1H-pentaleno[1,2-c]pyrrole-1,3-(2H)-dione The title compound was prepared from 10 mmoles each of 1-(4-aminobutyl)-4-(2-pyrazinyl)piperzine and octahydro-4,5,7-methenopentaleno-[1,2-c]furan-1,3-dione by refluxing 300 mL. of xylene under a nitrogen atmosphere for 48 hours with water removal via a Dean-Stark trap. The solvent was then removed in vacuo and the residue carefully column chromatographed on 250 g. of silica gel using a gradient elution starting with chloroform and ending with 5% ethanol in chloroform. The more polar major product was recrystallized from isopropanol with the addition of 4N HCl/isopropyl alcohol to obtain 1.0 g. of white solid, m.p. 176°–179° C.

Analysis for: $C_{23}H_{29}N_5O_2.2HCl$: Calculated: C, 57.50; H, 6.50; N, 14.58. Found: C, 57.76; H, 6.70; N, 14.73.

EXAMPLE 6

2-[4-[4-(6-Chloro-2-pyrazinyl)-1-piperazinyl]butyl]hexahydro-4,6,7-metheno-1H-2-pyridine-1,3-(2H)-dione The title compound was prepared from 7.7 mmoles each of 1-(4-aminobutyl)-4-(6-chloro-2-pyrazinyl)piperazine and hexahydro-4,6,7-methenocyclopent[c]pyran-1,3-dione by refluxing in 300 mL. of xylene under a nitrogen atmosphere for 48 hours with water removal via a Dean-Stark trap. The solvent was then removed in vacuo and the residue carefully column chromatographed on 250 g. of silica gel using a gradient elution starting with chloroform and ending with 5% ethanol in chloroform. The product was recrystalized from isopropanol with the addition of 4N HCl/isopropyl alcohol to obtain 2.1 g. of white solid, m.p. 221°–222° C.

Analysis for: $C_{21}H_{26}N_5O_2Cl.HCl.\frac{1}{4}H_2O$: Calculated: C, 55.21; H, 6.07; N, 15.33. Found: C, 55.02; H, 5.88; N, 15.07.

EXAMPLE 7

2-[4-[4-(2-Pyrimidinyl)-1-piperazinyl]butyl]hexahydro-4,6,7-metheno-1H-2-pyridine-1,3-(2H)-dione The title compound was prepared from 10 mmoles each of 1-(4-aminobutyl)-4-(2-pyrimidinyl)piperazine and hexahydro-4,6,7-methenocyclopent[c]pyran-1,3-dione by refluxing in 300 mL. of xylene under a nitrogen atmosphere for 48 hours with water removal via a Dean-Stark trap. The solvent was then removed in vacuo and the residue carefully column chromatographed on 250 g. of silica gel using a gradient elution starting with chloroform and ending with 5% alcohol in chloroform. The product was recrystallized from isopropanol with the addition of 4N HCl/isopropyl alcohol to obtain 1.25 g. of a pale gray solid, m.p. 248°–250° C.

Analysis for: $C_{21}H_{27}N_5O_2.HCl.\frac{1}{4}H_2O$: Calculated: C, 59.71; H, 6.80; N, 16.58. Found: C, 59.78; H, 6.64; N, 16.48.

What is claimed is:

1. A compound of the formulae:

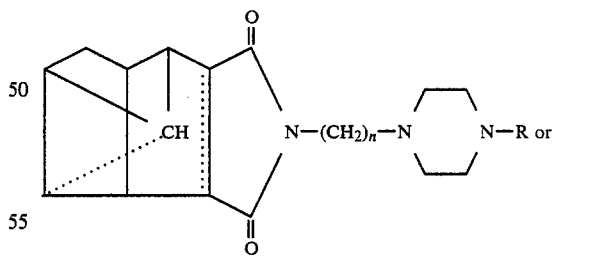

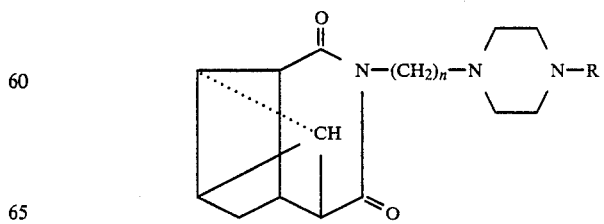

in which n is one of the integers 2, 3, 4 or 5;

R is phenyl, halophenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridinyl, halopyridin-2-yl, cyanopyridin-2-yl, quinolyl, or haloquinolyl;

and the dotted lines represent optional unsaturation; or a pharmaceutically acceptable salt thereof.

2. A compound of claim 1 which is endo-2-[4-[4-(2-pyrimidinyl)-1-piperazinyl]butyl]octahydro-4,5,7-metheno-1H-pentaleno[1,2-c]pyrrole-1,3-(2H)-dione, or a pharmaceutically acceptable salt thereof.

3. A compound of claim 1 which is exo-2-[4-[4-(2-pyrimidinyl)-1-piperazinyl]butyl]octahydro-4,5,7-metheno-1H-pentaleno[1,2-c]pyrrole-1,3-(2H)-dione, or a pharmaceutically acceptable salt thereof.

4. A compound of claim 1 which is endo-2-[4-[4-(6-chloro-2-pyrazinyl)-1-piperazinyl]butyl]octahydro-4,5,7-metheno-1H-pentaleno[1,2-c]pyrrole-1,3-(2H)-dione, or a pharmaceutically acceptable salt thereof.

5. A compound of claim 1 which is exo-2-[4-[4-(6-chloro-2-pyrazinyl)-1-piperazinyl]butyl]octahydro-4,5,7-metheno-1H-pentaleno[1,2-c]pyrrole-1,3-(2H)-dione, or a pharmaceutically acceptable salt thereof.

6. A compound of claim 1 which is endo-2-[4-[4-(2-pyrazinyl)-1-piperazinyl]butyl]octahydro-4,5,7-metheno-1H-pentaleno[1,2-c]pyrrole-1,3-(2H)-dione, or a pharmaceutically acceptable salt thereof.

7. A compound of claim 1 which is 2-[4-[4-(6-chloro-2-pyrazinyl)-1-piperazinyl]butyl]hexahydro-4,6,7-metheno-1H-2-pyrindine-1,3-(2H)-dione, or a pharmaceutically acceptable salt thereof.

8. A compound of claim 1 which is 2-[4-[4-(2-pyrimidinyl)-1-piperazinyl]butyl]hexahydro-4,6,7-metheno-1H-2-pyrindine-1,3-(2H)-dione, or a pharmaceutically acceptable salt thereof.

* * * * *